US00PP34771P2

(12) United States Plant Patent
Chaparro

(10) Patent No.: US PP34,771 P2
(45) Date of Patent: Nov. 29, 2022

(54) PEACH TREE NAMED 'UFSOL'

(50) Latin Name: *Prunus persica*
Varietal Denomination: 'UFSol'

(71) Applicant: Florida Foundation Seed Producers, Inc., Marianna, FL (US)

(72) Inventor: Jose X. Chaparro, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 14 days.

(21) Appl. No.: 17/803,263

(22) Filed: Apr. 8, 2022

(51) Int. Cl.
*A01H 6/74* (2018.01)
*A01H 5/08* (2018.01)

(52) U.S. Cl.
USPC ..... Plt./197

(58) Field of Classification Search
USPC ..... Plt./197
See application file for complete search history.

(56) References Cited

U.S. PATENT DOCUMENTS

PP21,607 P3 1/2011 Chaparro et al.
PP25,129 P3 12/2014 Chaparro et al.

*Primary Examiner* — Annette H Para
(74) *Attorney, Agent, or Firm* — Katherine Koenig; Koenig IP Works, PLLC

(57) ABSTRACT

A new and distinct cultivar of peach tree plant named 'UFSol'. This new cultivar has a low winter chilling requirement estimated at 200 chill units (cu). The tree is medium size, moderately vigorous, and semi-spreading in growth habit. It bears showy, light pink flowers, and leaves have reniform glands. Trees of 'UFSol' are self-fertile and regularly bear heavy annual crops of early season fruit that are of large size for its ripening season. Fruit are uniformly firm and yellow with non-melting, clingstone flesh. Fruit are nearly slightly oval, and uniform with a substantially symmetrical shape, have an attractive golden yellow skin. The fruit of 'UFSol' ripen in approximately the third week in April in Gainesville, Fla.

3 Drawing Sheets

Genus and species: *Prunus persica.*
Cultivar denomination: 'UFSol'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The present invention relates to a new and distinct cultivar of peach (*Prunus persica* (L.) Batsch) tree adapted to a subtropical (low chill) winter climate. This new tree, hereinafter referred to by the name 'UFSol', produces clingstone fruit with 0% red blush, of good eating quality, and that have non-melting flesh fruit for fresh market in late April in Gainesville, Fla. The new peach cultivar 'UFSol' is a promising candidate for commercial success in that it has large, sweet fruit with an attractive yellow peel color, and that ripen evenly and set fruit under the high night temperatures during bloom in central Florida.

'UFSol' peach tree (genotype) originated in a cultivated area of the fruit breeding program at the University of Florida, located in Gainesville, Fla., where it was tested. 'UFSol' was selected in 2009 because it exhibited tree and fruit qualities with potential for variety release. 'UFSol' was asexually propagated by budding onto 'Flordaguard' (unpatented) seedling rootstock (for root-knot nematode control) and determined to have unique tree and fruit characteristics making it worthy for commercial fresh fruit production. There are no known effects of this standard rootstock on this scion cultivar. Asexually propagated plants remained true to the original tree and all characteristics of the tree and the fruit have transmitted for two generations.

Plant Breeder's Rights for this cultivar have not been applied for. The new peach cultivar 'UFSol' has not been made publicly available more than one year prior to the filing of this application.

SUMMARY OF THE INVENTION

'UFSol' peach tree is a new and distinct variety that bears fruit that ripen in late April in Gainesville, Fla., and has a moderately low chilling dormancy requirement. 'UFSol' has showy light pink flowers . The estimated chilling requirement is 200 chill units, based on bloom time. 'UFSol' produces fruit that are clingstone and of good flavor and eating quality. The trees are vigorous, productive, and without alternate bearing. Trees attain in two years a height of two meters and a spread of one and a half meters in Gainesville, Fla. Terminal growth of up to a meter annually is common on mature five-year-old trees with normal pruning to a vase shape.

The first fruit of 'UFSol' ripen in late April in Gainesville, Fla., in about 69 days from full bloom. The fruit are uniformly large in size, averaging 133 g when properly thinned to a full crop. Ripe fruit have no red pigment in the flesh or at the pit.

Plant of the new peach cultivar 'UFSol' can be compared to plants of 'UFBest' (U.S. Plant Pat. No. 25,129), a standard peach variety. In side-by-side comparisons conducted in Gainesville, Fla., plants of the new peach cultivar 'UFSol' differed from plants of 'UFBest' in the following characteristics:

1. trees of 'UFSol' are more open than trees of 'UFBest';
2. flowers of 'UFSol' bloom about three to five days after those of 'UFBest';
3. first fruit of 'UFSol' typically ripen later than those of 'UFBest' (0-3 days after 'UFBest' in most years); and
4. skin of fruit of 'UFSol' has slightly shorter pubescence than skin of fruit of 'UFBest'.

DESCRIPTION OF THE FIGURES

The accompanying photographs (as shown in FIGS. 1-3) illustrate the overall appearance of the new peach cultivar 'UFSol' These photographs show the colors as true as can be reasonably obtained in colored reproductions of this type. Colors in the photographs may differ slightly from the color values cited in the detailed botanical description, which accurately describe the colors of the new peach cultivar.

DETAILED BOTANICAL DESCRIPTION OF THE CULTIVAR

Figure 1:
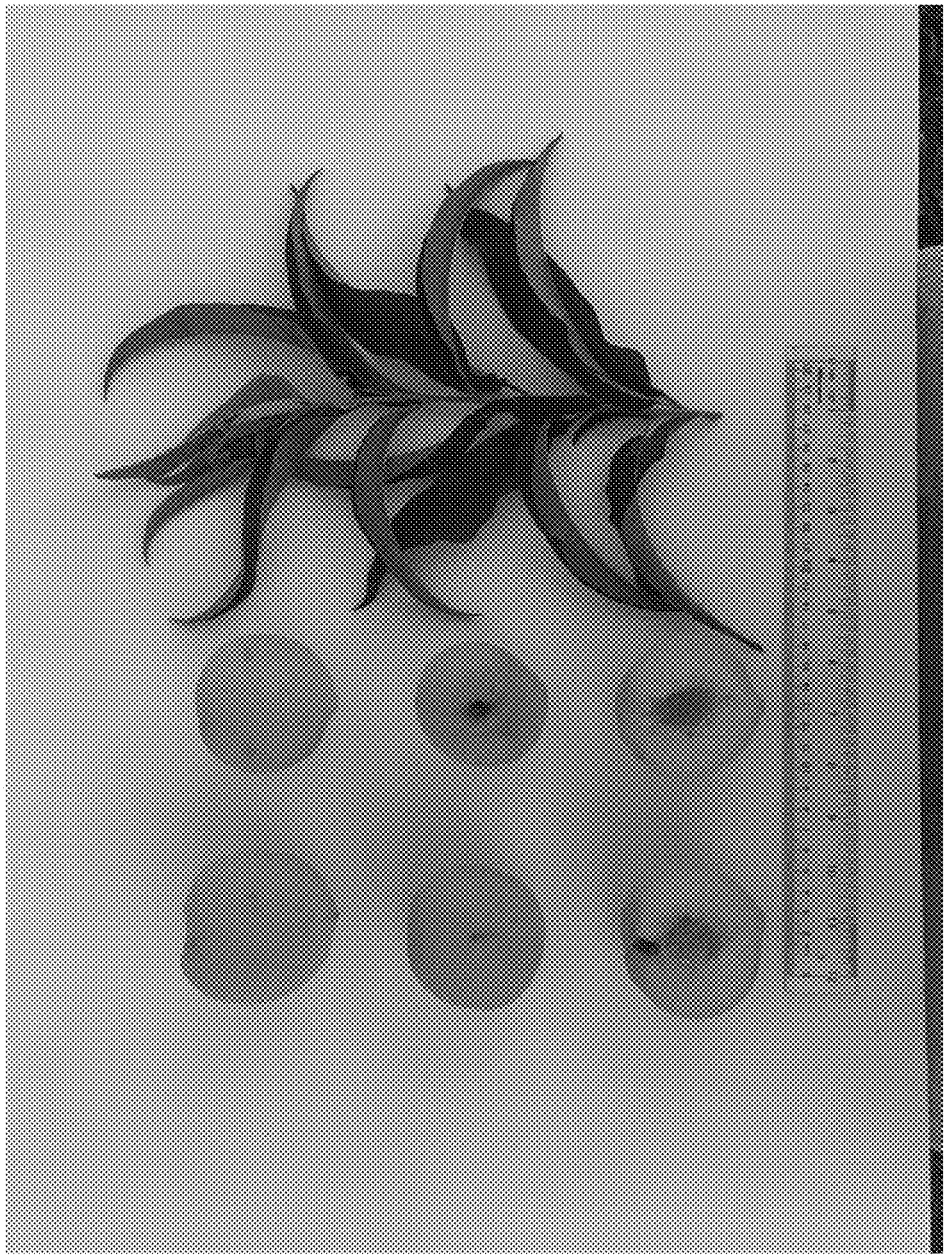
FIG. 1 shows a various views of the fruit (side view, stem end view, blossom end view, side views showing the structure of a fruit cut longitudinally to show the fruit with and without the pit) and mature leaves of the new peach cultivar 'UFSol'.
Figure 2:
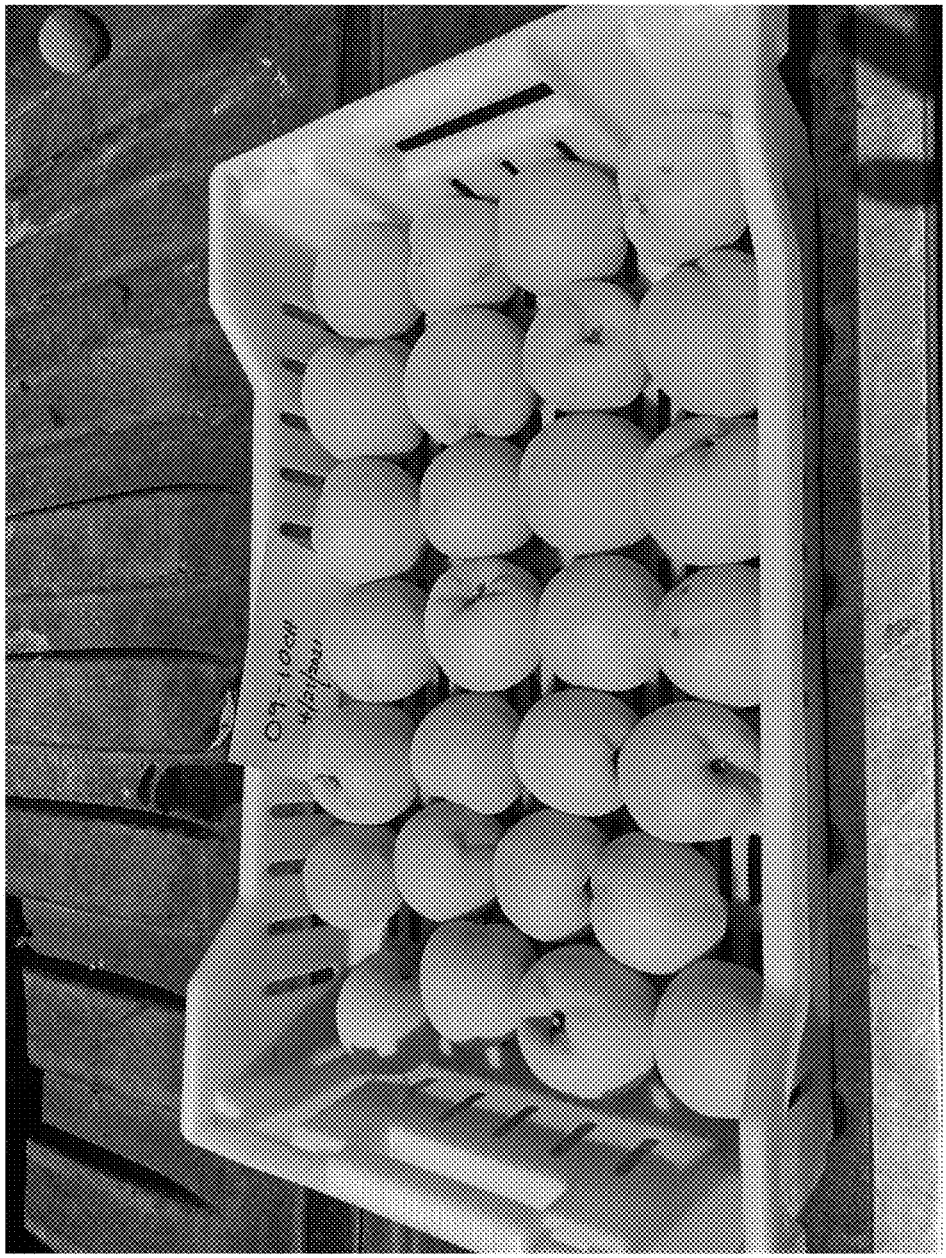
FIG. 2 shows an additional view of the fruit of the new peach cultivar 'UFSol'.
Figure 3:
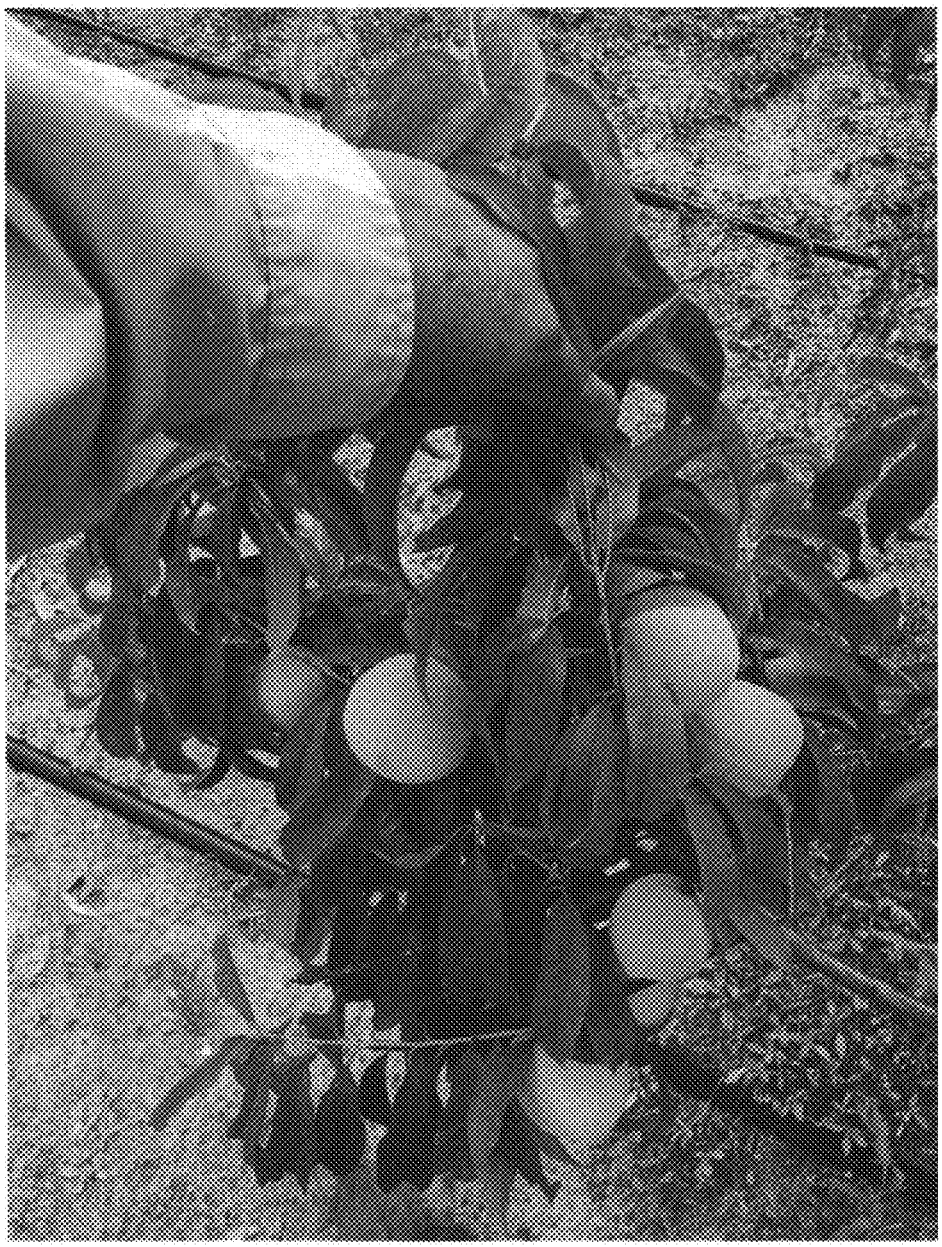
FIG. 3 shows a close-up view of a branch of a fruiting tree of the new peach cultivar 'UFSol' grown in a ground bed in full sun in Gainesville, Fla.

The following detailed description sets forth the distinctive characteristics of the new peach cultivar 'UFSol'. The present botanical description is that of the new cultivar grown as a five-year-old trees on 'Flordaguard' rootstock under the ecological conditions prevailing in Gainesville, Fla. The tree, flowers, and fruit of 'UFSol' may vary slightly in detail due to variations in soil type, cultural practices, and climatic condition. The potential for commercial production of fresh fruit by 'UFSol' is high, due to its attractive yellow fruit over a bright yellow ground color in the skin, large size fruit of good flavor, and good firmness with even ripening throughout the fruit. In the following description, color references are made to "The Pantone Book of Color," published by H. N. Abrams, Inc., N.Y. (1990), except where general terms of ordinary dictionary significance are used.

Botanical Description

Botanical classification:

*Family*.—Rosaceae.

*Botanical name*.—*Prunus persica*.

*Common name*.—Peach.

*Cultivar*.—'UFSol'.

Parentage:

*Female or seed parent*.—'UFOne' (U.S. Plant Pat. No. 21,607).

*Male or pollen parent*.—'AP01-02h' (unpatented).

Plant description:

*Type*.—Tree.

*Ploidy*.—Diploid.

*Plant form*.—Semi-spreading, but easily pruned to a vase shape.

*Plant size*.—Trees are medium in stature when trained to an open vase form.

*Vigor*.—Moderately vigorous, and must be pruned in summer and winter when grown to a vase shape to keep the tree open to get strong fruiting wood in the lower center. Trees typically respond to irrigation and fertilization. Tree growth of 4-6 feet in height and 3-5 feet in width occurs in the first growing season in the field in Gainesville, Fla., where they need summer pruning.

*Density*.—Light to medium in branching habit. Pruning in summer and winter is required to open the tree center and permit sunlight entrance for enhanced fruit color and sugar content development.

*Hardiness*.—Hardy with respect to typical north central Florida winters.

*Bearing*.—Productive annually without alternate bearing observed. Trees are self-fertile and must be fruit thinned to avoid limb breakage and to obtain large fruit size. Trees annually set several times the number of fruit for a desired crop load.

*Chilling requirement*.—Estimated endodormancy chilling requirement is 200 chill units based on the time of bloom and leafing in relation to standard varieties.

*Trunk*.—Size: Medium, trunk attaining a diameter of 8 cm at a height of 30 cm at the end of four years of growth in Gainesville, Fla. Texture: Medium smooth, but changes to medium shaggy as tree ages. Bark color: Older bark is gray (Chinchilla, Pantone 17-1109). Lenticels: Size: Medium small (2-8 mm in length perpendicular to the trunk). Color: Brown (Lark, Pantone 16-1324) with the center being yellowish brown (Medal Bronze, Pantone 17-0942).

*Branches*.—Size: Strong growth of scaffold branches. Fruiting branches are mostly of large diameter (4-10 mm) and not overly twiggy, resulting in strong fruiting wood. Thus, the tree growth and structure permit easier and faster winter pruning. Texture: Relatively smooth, numerous lenticels attaining size smaller than found on the trunk and old scaffolds (small-medium in size, 5-11 mm). Roughness increases with age. Color: New wood, summer: Light green (Mellow Green, Pantone 12-0426). Old fruiting wood, winter: Brown (Cinnamon, Pantone 19-1436). Crotch angles: Angles are selected at 45° to near 90° in first year of tree training. Natural angles are within the normal range of standard varieties for a spreading tree.

Foliage:

*Arrangement*.—Alternate.

*Size*.—Medium; 15-17 cm in length, including the petiole; 3.5-3.8 cm in width. Measurements were made on vigorous upright shoots of summer growth.

*Thickness*.—Average for commercial peach varieties. Not noticeably unusual.

*Form*.—Lanceolate.

*Apex*.—Acute.

*Margin*.—Serrulate, slightly undulate.

*Base*.—Cuneate.

*Surface*.—Upper surface: Glabrous. Lower surface: Lower surface has medium-large veins that are pinnately netted.

*Color*.—Lower surface: Green (Green Olive, Pantone 17-0535). Upper surface: Slightly darker green (Loden Green, Pantone 18-0422).

*Glands*.—Number: Usually two, small reniform glands mostly on lower leaf blade, but occasionally on petiole. Color: Leaf glands on young leaves are yellowish green (Sulphur, Pantone 14-0755).

*Petiole*.—Size: Averages 1.2 cm in length and 2 mm in diameter. Color: Light green (Moss, Pantone 16-0532) on older leaves of summer. Shape: Grooved longitudinally.

*Stipules*.—Number and size: Medium (equal to most commercial peach varieties), usually two per bud and abscising just before leaf becomes full size in summer growth. Color: Color at full size is green (Leek Green, Pantone 15-0628).

Inflorescence:

*Flower buds*.—Hardiness: Hardy with respect to north central Florida winters (16° F. minimum temperature observed). Abundance: Very high. Most buds set fruit in absence of spring frosts and show little evidence of bud drop. Size: Medium, averages 5 mm in length in mid-winter. Form: Plump, conic, and free. Surface: Pubescent scales. Color: Brown (Stucco, Pantone 16-1412) in late summer

*Flowers*.—Blossom period: Averages 50% bloom in late January most years in Gainesville, Fla., but occurring over a 7-10 day period. Time and length of bloom are dependent on ambient temperature. Aroma: None observed. Flower density: Abundant, varying one to three per node, but typically two per node. Type: Showy, location and seasonally variable within the range of commercial showy varieties. Flower diameter: Averages 4.2-5.0 cm. Petals: Number: Five. Size: Averages 23 mm in length and 13-14 mm in width. Texture: Smooth, glabrous. Margins: Undulate and wavy. Color: Light pink (Chalk, Pantone 12-2902) at flower opening. Stamens and pistils: Sizes, shapes, and colors are within the range of standard commercial varieties. Sepals: Number: Five. Size: Averages 7 mm in length and 6 mm in width at the point of attachment to the calyx cup; rounded at the distal end. Texture: Pubescent. Color, interior: Green (Peridot, Pantone 17-0336). Color, exterior: Green (Lizard, Pantone 18-0629). Margins: Smooth pubescent margin. Pistils: Number: Typically one per flower. Form: Straight (without curls or curves) just prior to flower opening. Size: Averages 18 mm in length (from tip of stigma to base of ovary). Color: Light green (Pale Star, Pantone 12-0626). Pedicel: Size: 8-9 mm in length and approximately 3 mm in width. Color: Green (Mellow Green, Pantone 12-0426). Calyx cup: Size, form: Medium small, in the size range of commercial peach varieties. Size: 7 mm in diameter at the time of flower opening. Color, exterior: Red (Deep Red Brown, Pantone 19-1321). Color, interior: Red (Burnt Sienna, Pantone 17-1544). Stamen: Anthers, number: Varies from 38-54. Anthers, color: Orange (Pumpkin, Pantone 14-1139) al flower opening. Filament, length: 13-15 mm. Filament, color: Light pink (Cameo Pink, Pantone 14-2307). Pollen: Presence: Abundant. Color: Bright yellow (Cornsilk, Pantone 13-0932). Fertility: Fully self-fertile, and no cross-pollination is required. Fruit set is abundant.

Fruit:

*Maturity when described*.—Tree ripe, Apr. 15, 2021, in Gainesville, Fla.

*Date of picking*.—First picking on Apr. 15, 2021, in Gainesville, Fla.; last picking on Apr. 21, 2021, in Gainesville, Fla.

*Size*.—Uniform, medium large (large size for early mid-season maturity at 130-150 g). Size varies with fruit number per tree, soil type, climatic conditions, and cultural practices. Average equatorial diameter: 2.5 in (63 mm). Average polar length (stem to distal end): 2.5 in (63 mm).

*Longitudinal section form*.—Nearly round with slight tip.

*Transverse section form, through diameter*.—Nearly round with slight suture bulge.

*Suture*.—Shallow and inconspicuous except for a slight crease on the stem end of the fruit.

*Ventral surface*.—Mostly rounded with a slight suture bulge on one side.

*Base*.—Slightly cordate.

*Apex*.—Slightly obtuse.

*Crater at stem attachment*.—Form: Flaring circular with slight suture crease at the stem end. Size: 9-11 mm in depth, 20 mm in breadth at the top, 5 mm at pedicel attachment.

*Skin*.—Thickness: Medium in comparison to commercial peach varieties. Texture: Medium in comparison to commercial peach varieties. Tenacity: Tenacious to flesh. Color: Yellow (Radiant Yellow, Panton 15-1058) over 100% of the skin. Tendency to crack: None observed. Taste: No astringency observed. Epidermis: Pubescent.

*Flesh*.—Ripening: Even ripening within each fruit. Texture: Firm, juicy, non-melting when fully ripe. Fibers: Very fine, small, tender, and abundant. Aroma: Moderate and in the middle range of commercial peach varieties. Eating quality: Good, moderately sweet, slightly acid. Soluble solids vary from 10.6-13.6 brix at 2.5-3.0 kg penetrometer firmness with a 3/16 inch tip over a five-year period (the years 2011 and 2013-2016). Juice: Abundant. Color: Yellow (Daffodil, Pantone 14-0850). There is no red at the pit. Browning by oxidation: Not detectable on tree ripe fruit beginning to soften. Amygdalin: Undetected.

*Stone*.—Type: Clingstone. Size: Medium-small. Averages 28 mm in length, 20 mm in width, 16 mm in thickness, and 5 mm in wall thickness. Color: Light brown (Buff, Pantone 13-1024) when flesh is freshly cut. Form: Oblong. Base: Straight. Apex: Acute, but with no sharp apex. Sides: Near equal. Surface: Slightly irregularly furrowed and pitted from base to apex. Ridges: Not prominent. Tendency to split: None observed. Seed: Amygdalin: Abundant (kernel is bitter). Viability: Viable if stratified upon removal from fruit at harvest and without drying. Color: Kernel is white (Winter White, Pantone 11-0507) when first removed from ripe fruit. Size: 14 mm in length, 10 mm in width, 5 mm thick. Shape: Acute tip with obtuse base and overall ovate shape.

*Use*.—Fresh; dessert.

Resistance to diseases and pests: High leaf and fruit resistance to bacterial spot incited by *Xanthomonas campestris* pv. *pruni* (Pers.) Diet. Resistance to other fruit and tree diseases are within the range for commercial peach cultivars in Florida. No unusual resistance or susceptibility to insects and diseases noted.

Keeping quality: Excellent after eight days at 2° C. and with minimal bruises or scarring appearing on skin.

Shipping quality: Degree of firmness at harvest and firmness retained in refrigeration for eight days at 2° C., with no internal breakdown of flesh or appreciable loss of eating quality, which indicates fruit should be highly acceptable for shipping.

I claim:

1. A new and distinct tree named 'UFSol' as illustrated and described herein.

* * * * *